US008632730B2

(12) United States Patent
Petrilla et al.

(10) Patent No.: US 8,632,730 B2
(45) Date of Patent: Jan. 21, 2014

(54) ASSAYING TEST STRIPS HAVING DIFFERENT CAPTURE REAGENTS

(75) Inventors: John F. Petrilla, Palo Alto, CA (US); Daniel B. Roitman, Menlo Park, CA (US)

(73) Assignee: Alverix, Inc., San Jose, CA (US)

( * ) Notice: Subject to any disclaimer, the term of this patent is extended or adjusted under 35 U.S.C. 154(b) by 843 days.

(21) Appl. No.: 11/285,413

(22) Filed: Nov. 22, 2005

(65) Prior Publication Data

US 2007/0116595 A1   May 24, 2007

(51) Int. Cl.
*G01N 21/75* (2006.01)

(52) U.S. Cl.
USPC ........... 422/400; 422/401; 422/402; 422/404; 422/405; 422/406; 422/408; 422/409; 422/410; 422/413; 422/419; 422/420; 422/421; 422/422; 422/423; 422/424; 422/425; 422/426; 422/427; 422/428; 422/429; 422/430; 422/50; 422/500; 422/63; 422/66; 422/68.1; 422/82.01; 422/82.05; 422/82.06; 422/560; 422/561; 422/562; 422/563; 436/164; 436/169; 436/170; 436/44; 435/13; 435/283.1; 435/287.1; 435/287.7; 435/287.8; 435/287.9; 435/288.7; 204/403.02; 206/363; 221/135; 221/2; 221/232; 221/268; 221/270; 221/65; 222/511; 361/727; 403/24; 424/63; 600/309; 600/365; 600/573; 600/583; 600/584; 606/182; 73/53.01

(58) Field of Classification Search
USPC ........ 422/58, 82.05, 400, 401, 402, 404, 405, 422/406, 408, 409, 410, 413, 419, 420, 421, 422/422, 423, 424, 425, 426, 427, 428, 429, 422/430, 50, 500, 63, 66, 68.1, 82.01, 422/82.06, 560, 561, 562, 563; 436/164, 436/44, 46, 169, 170; 435/13, 283.1, 287.1, 435/287.7, 287.8, 287.9, 288.7; 73/53.01
See application file for complete search history.

(56) References Cited

U.S. PATENT DOCUMENTS

| | | | | |
|---|---|---|---|---|
| 3,907,503 A | * | 9/1975 | Betts et al. | 422/67 |
| RE28,803 E | * | 5/1976 | Durkos et al. | 702/25 |
| 5,426,384 A | * | 6/1995 | May | 327/52 |
| 5,861,256 A | | 1/1999 | Glass et al. | |
| 6,136,610 A | | 10/2000 | Polito et al. | |

(Continued)

FOREIGN PATENT DOCUMENTS

WO   WO 2004077028 A1 *   9/2004

OTHER PUBLICATIONS

"Immunochromatographic, Lateral Flow or Strip Tests Development Ideas," Bangs Laboratories, Inc., downloaded from http://www.pall.com/34445_4154.asp, 7 pages (1998).

*Primary Examiner* — Dennis M White
(74) *Attorney, Agent, or Firm* — K&L Gates LLP (57) ABSTRACT

In one aspect, a diagnostic test system includes a receptacle, optical detectors, and a logic circuit. Each of the optical detectors has a corresponding view in the receptacle and produces an electrical signal at a respective detector output in response to light from the corresponding view. The logic circuit includes logic inputs that are respectively coupled to the detector outputs and that produce an output logic signal corresponding to a logical combination of signals received at the logic inputs. In another aspect, respective detection signals are produced in response to light received from respective ones of multiple views of the test strip, and at least one output logic signal corresponding to a respective logical combination of the detection signals is generated.

12 Claims, 6 Drawing Sheets

(56) References Cited

U.S. PATENT DOCUMENTS

| | | |
|---|---|---|
| 6,268,162 B1 | 7/2001 | Phillips et al. |
| 6,483,582 B2 | 11/2002 | Modlin et al. |
| 6,630,307 B2 | 10/2003 | Bruchez et al. |
| 2003/0119202 A1 | 6/2003 | Kaylor et al. |
| 2003/0119203 A1 | 6/2003 | Wei et al. |
| 2003/0207454 A1 | 11/2003 | Eyster et al. |
| 2004/0018637 A1 | 1/2004 | Polito et al. |
| 2004/0043502 A1 | 3/2004 | Song et al. |
| 2004/0151632 A1 | 8/2004 | Badley et al. |
| 2006/0197955 A1* | 9/2006 | Koike .......................... 356/446 |

* cited by examiner

ASSAYING TEST STRIPS HAVING DIFFERENT CAPTURE REAGENTS

CROSS-REFERENCE TO RELATED APPLICATIONS

This application also is related to the following co-pending applications, each of which is incorporated herein by reference: U.S. patent application Ser. No. 11/112,807, filed Apr. 22, 2005, by Patrick T. Petruno et al. and entitled "LATERAL FLOW ASSAY SYSTEMS AND METHODS;" U.S. patent application Ser. No. 10/816,636, filed Apr. 1, 2004, by Patrick T. Petruno et al., and entitled "OPTOELECTRONIC RAPID DIAGNOSTIC TEST SYSTEM;" U.S. patent application Ser. No. 11/044,394, filed Jan. 26, 2005, by Patrick T. Petruno et al., and entitled "OPTOELECTRONIC RAPID DIAGNOSTIC TEST SYSTEM;" U.S. patent application Ser. No. 11/280,640, filed Nov. 16, 2005, by Patrick T. Petruno et al. and entitled "ASSAY TEST STRIPS AND READING SAME".

BACKGROUND

Figure 1:
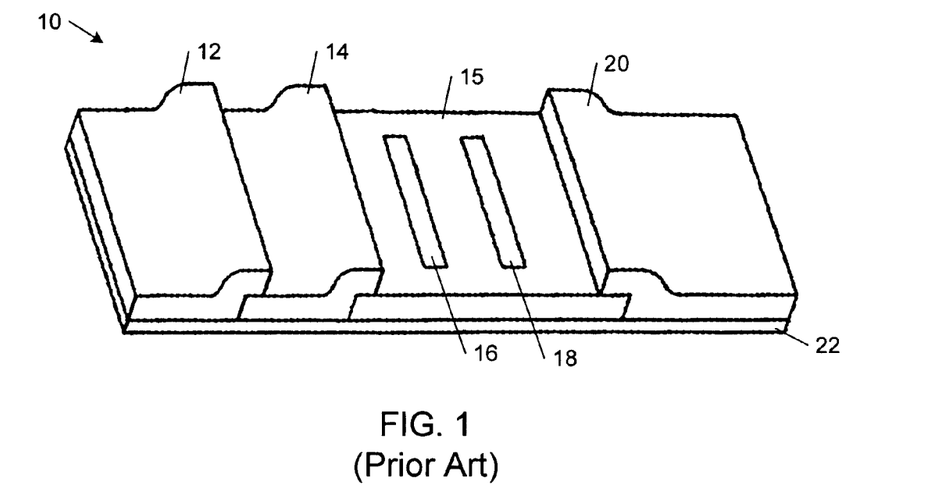
FIG. 1 is a diagrammatic view of a prior art implementation of an assay test strip.

Assay test kits are currently available for testing a wide variety of medical and environmental conditions or compounds, such as a hormone, a metabolite, a toxin, or a pathogen-derived antigen. FIG. 1 shows a typical lateral flow test strip 10 that includes a sample receiving zone 12, a labeling zone 14, a detection zone 15, and an absorbent zone 20 on a common substrate 22. These zones 12-20 typically are made of a material (e.g., chemically-treated nitrocellulose) that allows fluid to flow from the sample receiving zone 12 to the absorbent zone 22 by capillary action. The detection zone 15 includes a test region 16 for detecting the presence of a target analyte in a fluid sample and a control region 18 for indicating the completion of an assay test.

Figure 2A:
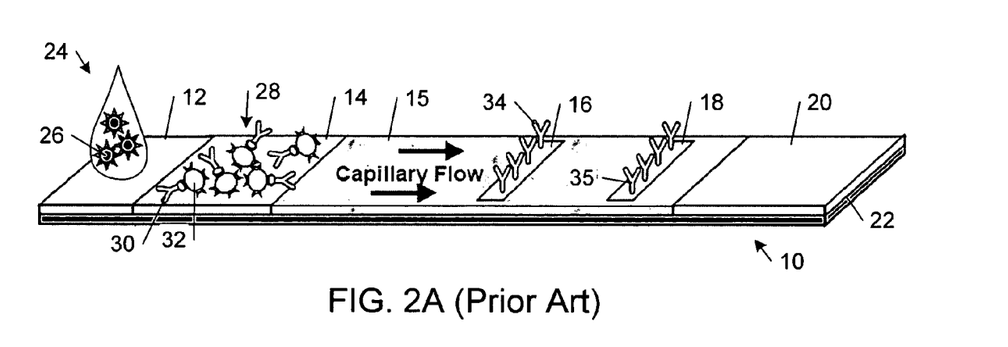
FIG. 2A is a diagrammatic view of a fluid sample being applied to a sample receiving zone of the assay test strip shown in FIG. 1.
Figure 2B:
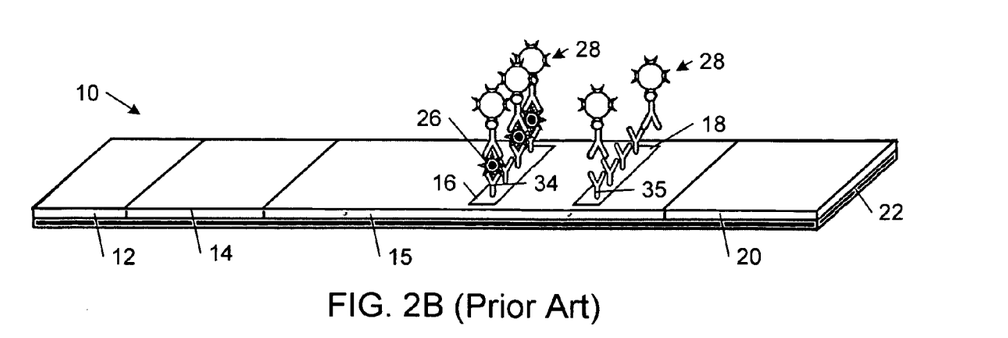
FIG. 2B is a diagrammatic view of the assay test strip shown in FIG. 2A after the fluid sample has flowed across the test strip to an absorption zone.

FIGS. 2A and 2B show an assay performed by an exemplary implementation of the test strip 10. A fluid sample 24 (e.g., blood, urine, or saliva) is applied to the sample receiving zone 12. In the example shown in FIGS. 2A and 2B, the fluid sample 24 includes a target analyte 26 (i.e., a molecule or compound that can be assayed by the test strip 10). Capillary action draws the liquid sample 24 downstream into the labeling zone 14, which contains a substance 28 for indirect labeling of the target analyte 26. In the illustrated example, the labeling substance 28 consists of an immunoglobulin 30 with a detectable particle 32 (e.g., a reflective colloidal gold or silver particle). The immunoglobulin 30 specifically binds the target analyte 26 to form a labeled target analyte complex. In some other implementations, the labeling substance 28 is a non-immunoglobulin labeled compound that specifically binds the target analyte 26 to form a labeled target analyte complex.

The labeled target analyte complexes, along with excess quantities of the labeling substance, are carried along the lateral flow path into the test region 16, which contains immobilized compounds 34 that are capable of specifically binding the target analyte 26. In the illustrated example, the immobilized compounds 34 are immunoglobulins that specifically bind the labeled target analyte complexes and thereby retain the labeled target analyte complexes in the test region 16. The presence of the labeled analyte in the sample typically is evidenced by a visually detectable coloring of the test region 16 that appears as a result of the accumulation of the labeling substance in the test region 16.

The control region 18 typically is designed to indicate that an assay has been performed to completion. Compounds 35 in the control region 18 bind and retain the labeling substance 28. The labeling substance 28 typically becomes visible in the control region 18 after a sufficient quantity of the labeling substance 28 has accumulated. When the target analyte 26 is not present in the sample, the test region 16 will not be colored, whereas the control region 18 will be colored to indicate that assay has been performed. The absorbent zone 20 captures excess quantities of the fluid sample 24.

In the non-competitive-type of lateral flow assay test strip designs shown in FIGS. 2A and 2B, an increase in the concentration of the analyte in the sample results in an increase in the concentration of labels in the test region. Conversely, in competitive-type of lateral flow assay test strip designs, an increase in the concentration of the analyte in the fluid sample results in a decrease in the concentration of labels in the test region.

Lateral flow assay test strips may include multiple test regions that include different respective immobilized compounds that specifically bind different respective target analytes. Pall Corporation has published an article entitled "Immunochromatographic, Lateral Flow or Strip Tests Development Ideas" that proposes that such test strips might be used to create a visually-detectable drugs-of-abuse test and visually-detectable panels for which multiple analytes can be tested, such as immune diseases, allergies, or even Multiple Chemical Sensitivity Disorder.

Although visual inspection of lateral flow assay devices of the type described above are able to provide qualitative assay results, such a method of reading these types of devices is unable to provide quantitative assay measurements and therefore is prone to interpretation errors. Automated and semi-automated lateral flow assay readers have been developed in an effort to overcome this deficiency. These readers typically include a light source and one or more sensors that detect the intensity of light from the labels that are immobilized in the capture regions (e.g., the test and control regions) of the test strip. Many of these readers determine the concentrations of the target analytes in the sample by measuring the intensities of the light signals from each test region and subsequently quantifying the measured light signals with respect to a baseline signal or a calibration signal that is obtained from one or more calibration regions on the test strip. Such readers require significant computing and processing resources to determine single-factor (i.e., concentrations of individual target analytes) assays of test samples.

What are needed are systems and methods of performing rapid, low-cost multifactor assays, such as multi-analyte screening tests, on test strips that have multiple capture reagents.

SUMMARY

In one aspect, the invention features a diagnostic test system that includes a receptacle, optical detectors, and a logic circuit. Each of the optical detectors has a corresponding view in the receptacle and produces an electrical signal at a respective detector output in response to light from the corresponding view. The logic circuit includes logic inputs that are respectively coupled to the detector outputs and that produce an output logic signal corresponding to a logical combination of signals received at the logic inputs.

In another aspect, the invention features a machine-implemented diagnostic test method in accordance with which respective detection signals are produced in response to light received from respective ones of multiple views of the test strip. At least one output logic signal corresponding to a respective logical combination of the detection signals is generated.

Other features and advantages of the invention will become apparent from the following description, including the drawings and the claims.

DETAILED DESCRIPTION

In the following description, like reference numbers are used to identify like elements. Furthermore, the drawings are intended to illustrate major features of exemplary embodiments in a diagrammatic manner. The drawings are not intended to depict every feature of actual embodiments nor relative dimensions of the depicted elements, and are not drawn to scale. Elements shown with dashed lines are optional elements in the illustrated embodiments incorporating such elements.

I. Introduction

The embodiments that are described in detail below provide systems and methods of performing rapid, low-cost multifactor assays on test strips that have different types of capture reagents. These embodiments enable test strips to be evaluated in terms of logical relationships among the detection results for different target analytes on a single test strip. Exemplary assays of this type include screening tests for drugs of abuse, screening tests for prescription medicines, and screening tests for multifactor clinical scenarios, such as diseases, allergies, and chemical sensitivities.

The terms "assay test strip" and "lateral flow assay test strip" encompass both competitive and non-competitive types of lateral flow assay test strips. A lateral flow assay test strip generally includes a sample receiving zone and a detection zone, and may or may not have a labeling zone. In some implementations, a lateral flow assay test strip includes a sample receiving zone that is located vertically above a labeling zone, and additionally includes a detection zone that is located laterally downstream of the labeling zone.

The term "analyte" refers to a substance that can be assayed by the test strip. Examples of different types of analytes include organic compounds (e.g., proteins and amino acids), hormones, metabolites, antibodies, pathogen-derived antigens, drugs, toxins, and microorganisms (e.g., bacteria and viruses).

As used herein the term "label" refers to a substance that has specific binding affinity for an analyte and that has a detectable characteristic feature that can be distinguished from other elements of the test strip. The label may include a combination of a labeling substance (e.g., a fluorescent particle, such as a quantum dot) that provides the detectable characteristic feature and a probe substance (e.g., an immunoglobulin) that provides the specific binding affinity for the analyte. In some implementations, the labels have distinctive optical properties, such as luminescence (e.g., fluorescence) or reflective properties, which allow regions of the test strip containing different labels to be distinguished from one another.

The term "reagent" refers to a substance that reacts chemically or biologically with a target substance, such as a label or an analyte.

The term "capture region" refers to a region on a test strip that includes one or more immobilized reagents.

The term "test region" refers to a capture region containing an immobilized reagent with a specific binding affinity for an analyte.

The term "control region" refers to a capture region containing an immobilized reagent with a specific binding affinity for a label.

The term "view" refers to an area that is visible to an optical detector. Among other things, a view is defined by the properties of the light that is detected by the optical detector. These properties are determined at least in part by the detection capabilities of the optical detector and by any optical elements, such as filters, mirrors, and lenses, that might filter, guide, and shape the light that reaches the optical detector.

II. Diagnostic Test System Architecture

A. Overview

Figure 3:
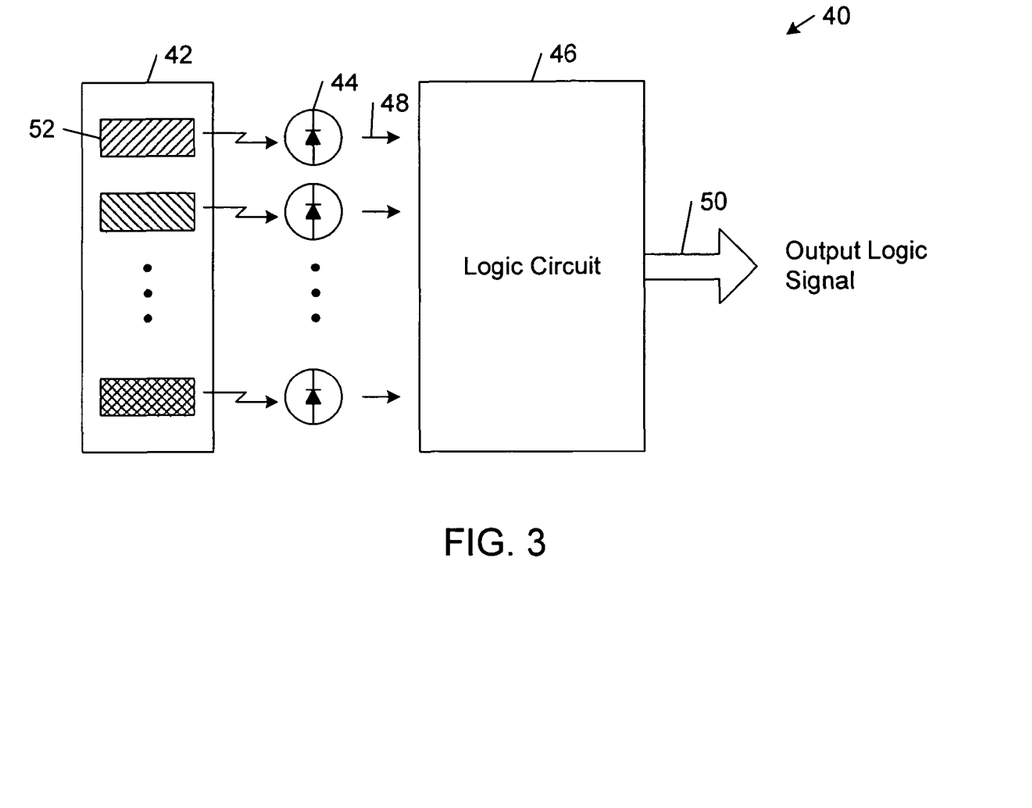
FIG. 3 is a schematic diagram of an embodiment of a diagnostic test system.

FIG. 3 shows an embodiment of a diagnostic test system 40 for assaying a test strip 42. The diagnostic test system 40 includes optical detectors 44 and a logic circuit 46. Each of the optical detectors 44 has a corresponding view of the test strip 42. In the illustrated embodiment, the test strip 42 has multiple capture regions 52, each of which has a respective immobilized reagent, and the view of each of the detectors 44 corresponds to at least a portion of a respective one of the capture regions 52. In other embodiments, one or more of the capture regions 52 may contain different capture reagents that specifically bind different respective labels that fluoresce in different respective wavelength ranges. With respect to these embodiments, multiple ones of the optical detectors 44 may have different views of the same capture region, where each view is defined by a different respective optical filter that selectively transmits light that is emitted from a respective one of the different labels that are immobilized in the capture region.

Figure 4:
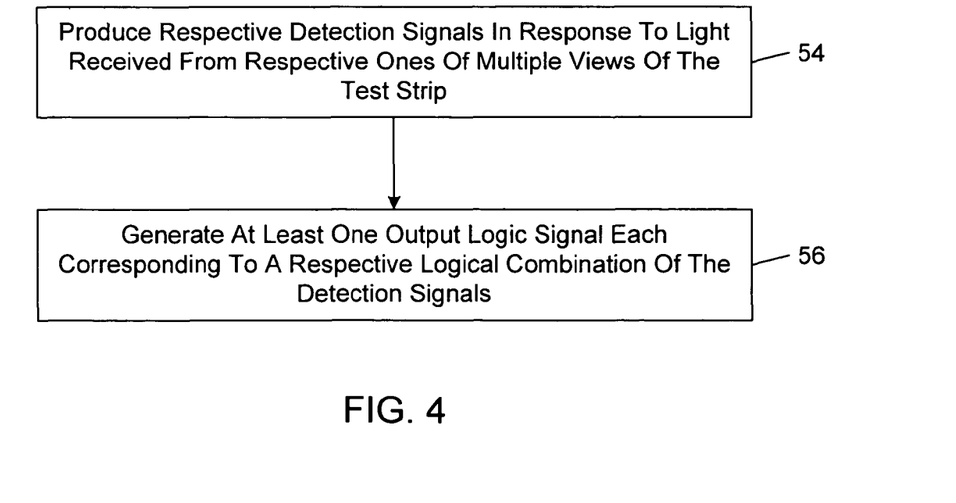
FIG. 4 is a flow diagram of an embodiment of a diagnostic test method.

FIG. 4 shows an embodiment of a diagnostic test method that is implemented by an embodiment of the diagnostic test system 40. In accordance with this method, respective detection signals are produced from electrical signals 48 that are produced by the optical detectors 44 (FIG. 4, block 54). The detection signals may correspond exactly to the electrical signals 48 or they may be derived from the electrical signals 48. The logic circuit 46 generates at least one output logic signal 50 each corresponding to a respective logical combination of the detection signals (FIG. 4, block 56). In this process, the logic circuit 46 evaluates a logical relationship among the detection results for different target analytes on a single test strip in accordance with a specified multifactor assay. Exemplary multifactor assays of this type include screening tests for drugs of abuse, screening tests for prescription medicines, screening tests for multi-analyte clinical scenarios, such as diseases, allergies, and chemical sensitivities.

Figure 5:
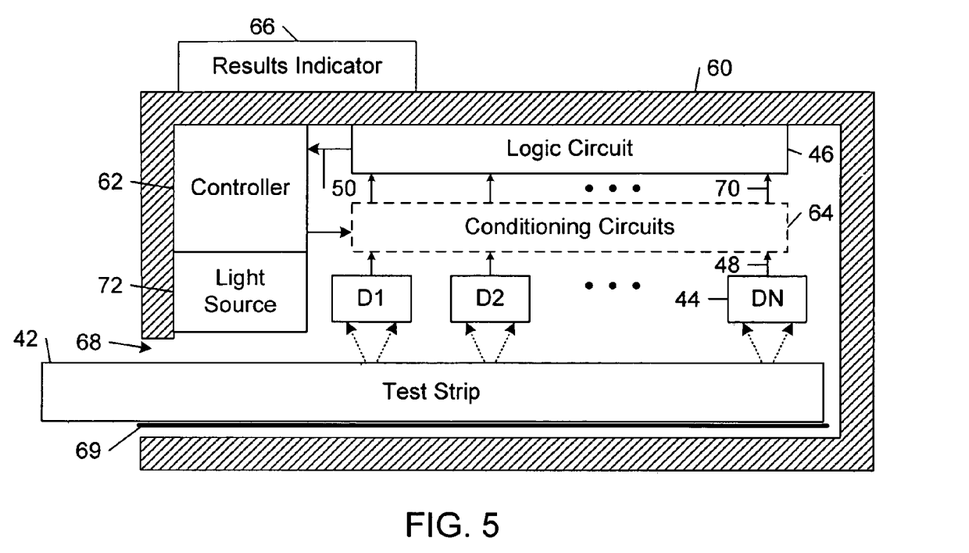
FIG. 5 is a block diagram of an embodiment of the diagnostic test system shown in FIG. 3.

FIG. 5 shows an embodiment 58 of the diagnostic test system 40 that includes a housing 60, N optical detectors 44 (D1, D2, . . . , DN, where N has an integer value greater than one), the logic circuit 46, a controller 62, optional conditioning circuits 64, and a results indicator 66. The housing 60 includes a receptacle 68 for receiving the test strip 42. When the test strip 42 is loaded in the receptacle 68, the optical detectors 44 produce electrical signals 48. The electrical signals typically are proportional to the intensities of light that are received by the optical detectors 44. In general, the light intensity measurements may be unfiltered or they may be filtered in terms of at least one of wavelength and polarization. The conditioning circuits 64, if present, condition (e.g., filter, scale, level-shift, quantize, or otherwise modify one or more properties of) the electrical signals 48 to produce respective detection signals 70. The logic circuit 46 determines at least one output logic signal 50 that corresponds to a logical combination of the detection signals 70. The results indicator 66 provides an indication of the values of the one or more output logic signals 50. In some implementations, the diagnostic test system 58 is fabricated from relatively inexpensive components enabling it to be used for disposable or single-use applications.

The housing 60 may be made of any one of a wide variety of materials, including plastic and metal. The housing 60 forms a protective enclosure for the optical detectors 44, the conditioning circuits 64 (if present), the logic circuit 46, the controller 62, a power supply (not shown), and other components of the diagnostic test system 58. The housing 60 also includes a holder 69, which mechanically registers the capture regions of the test strip 42 with respect to the optical detectors 44. The holder 69 may be stationary or movable in relation to the housing 60. The holder 69 may be designed to receive any one of a wide variety of different types of test strips 42, including test strips of the type shown in FIG. 1.

In the illustrated embodiments, each of the test strips 42 is a non-competitive type of assay test strip that supports lateral flow of a fluid sample along a lateral flow direction and includes a labeling zone containing labeling substances that bind respective labels to respective target analytes and a detection zone that includes multiple test regions, each of which contains a respective immobilized substance that binds a respective target analyte. Areas of the detection zone, including at least a portion of each of the test regions, are exposed for optical inspection by the optical detectors 44. The exposed areas of the detection zone may or may not be covered by an optically transparent window.

In other embodiments, the test strips are competitive type of lateral flow assay test strips in which the concentrations of the label in the test region decreases with increasing concentration of the target analyte in the fluid sample. Some of these embodiments include a labeling zone, whereas others of these implementations do not include a labeling zone.

Some of these competitive lateral flow assay test strip embodiments include a labeling zone that contains a label that specifically binds target analytes in the fluid sample, and a test region that contains immobilized target analytes as opposed to immobilized test reagents (e.g., antibodies) that specifically bind any non-bound labels in the fluid sample. In operation, the test region will be labeled when there is no analyte present in the fluid sample. However, if target analytes are present in the fluid sample, the fluid sample analytes saturate the label's binding sites in the labeling zone, well before the label flows to the test region. Consequently, when the label flows through the test region, there are no binding sites remaining on the label, so the label passes by and the test region remains unlabeled.

In other competitive lateral flow assay test strip embodiments, the labeling zone contains only pre-labeled analytes (e.g., gold adhered to analyte) and the test region contains immobilized test reagents with an affinity for the analyte. In these embodiments, if the fluid sample contains unlabeled analyte in a concentration that is large compared to the concentration of the pre-labeled analyte in the labeling zone, then label concentration in the test region will appear proportionately reduced.

In some embodiments, the housing 60 also contains at least one light source 72. In some implementations, the light source 72 includes a semiconductor light-emitting diode. Depending on the nature of the labels that are used by the test strip 42, the light source 72 may be designed to emit light within a particular wavelength range or light with a particular polarization. For example, if the labels are fluorescent labels, such as quantum dots, the light source 72 may be designed to illuminate the exposed areas of the detection zone of the test strip 42 with light in a wavelength range that induces fluorescent emission from the labels.

The optical detectors 44 include one or more optoelectronic components for optically inspecting the exposed areas of the detection zone of the test strip 42. In some implementations, the optical detectors 44 include respective photodetectors (e.g., semiconductor photodiodes). In some embodiments, the optical detectors are designed to selectively capture light from the capture regions in the detection zone. For example, if one or more of the labels on the test strip 42 are fluorescent labels, corresponding ones of the optical detectors 44 may be designed to selectively capture light within the respective wavelength ranges of the fluorescent light emitted by corresponding ones of the labels. On the other hand, if one or more of the labels are reflective-type labels, corresponding ones of the optical detectors may be designed to selectively capture light within the wavelength range or polarization of the light emitted by the light source 72. To these ends, the optical detectors 44 may include one or more optical filters that define the wavelength ranges or polarizations axes of the captured light.

The optional conditioning circuits 64 condition the electrical signals 48 to produce the detection signals 70 that are applied to the inputs of the logic circuit 46. The signal conditioning performed by the conditioning circuits 64 may include filtering noise from the electrical signals 48, scaling the current or voltage of the electrical signals 48, shifting the direct current levels of the electrical signals 48, quantizing the analog signals 48 into a binary (i.e., logic) signal, or otherwise modifying one or more properties of the electrical signals 48. The conditioning circuits 64 also may perform gating and reset functions that ensure that the detection signals 70 correspond to the desired measurements of light intensity from the test strip 42.

The controller 62 receives the one or more output logic signals 50 from the logic circuit 46, causes the results indicator 66 to provide an indication of the results of an assay of the test strip 42 that are reflected by the values of the one or more output logic signals 50, and controls any of the gating and reset functions that are performed by the conditioning circuits 64. In general, the controller 62 may be implemented in any computing or processing environment, including in digital electronic circuitry or in computer hardware, firmware, or software. In some embodiments, the controller 62 includes a processor (e.g., a microcontroller, a microprocessor, or ASIC) and an analog-to-digital converter. In the illustrated embodiment, the controller 62 is incorporated within the housing 62 of the diagnostic test system 58. In other embodiments, the controller 62 is located in a separate device, such as a computer, that may communicate with the diagnostic test system 58 over a wired connection or a wireless connection.

In general, the results indicator 66 may include any one of a wide variety of different mechanisms for indicating one or more results of an assay test. In some implementations, the results indicator 66 includes one or more lights (e.g., light-emitting diodes) that are activated to indicate, for example, a positive test result and the completion of the assay test (e.g., when sufficient quantity of labeling substance has accumulated in the control region). In other implementations, the results indicator 66 includes an alphanumeric display (e.g., a two or three character light-emitting diode array) for presenting assay test results.

A power supply supplies power to the active components of the diagnostic test system 58, including the optical detectors 44, the conditioning circuits 64 (if present), the logic circuit 46, the controller 62, the light source 72, and the results indicator 66. The power supply may be implemented by, for example, a replaceable battery or a rechargeable battery. In other embodiments, the diagnostic test system 58 may be powered by an external host device (e.g., a computer connected by a USB cable).

B. Exemplary Implementations of Diagnostic Test Systems

Figure 6:
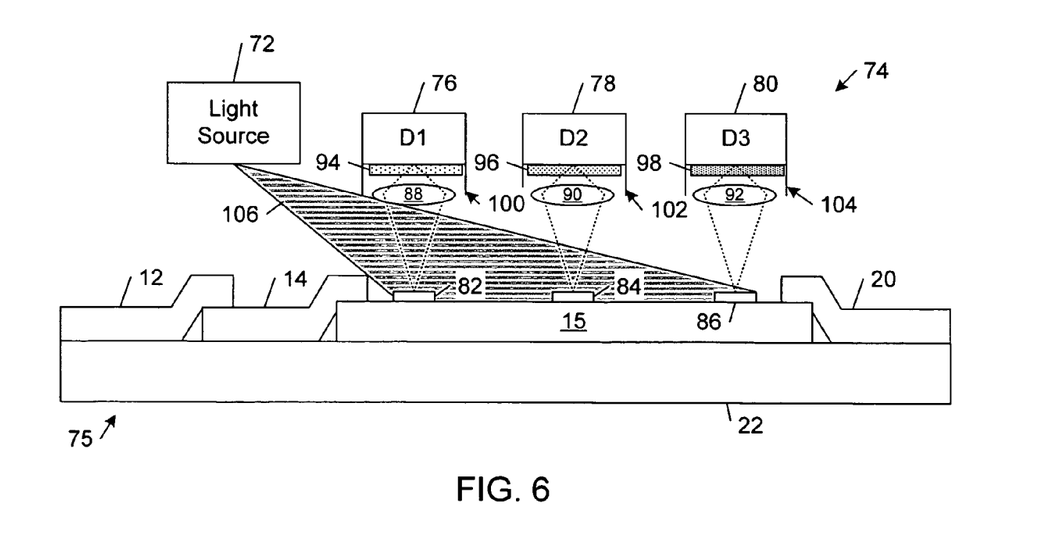
FIG. 6 is a diagrammatic side view of a portion of an embodiment of the diagnostic test system shown in FIG. 5.

FIG. 6 shows an exemplary embodiment 74 of the diagnostic test system 58 that is configured to assay an embodiment 75 of the test strip 42. The gross structural features of the test strip 75 are substantially the same as the corresponding features of the test strip 10, which is shown in FIG. 1. In particular, the test strip 42 includes the sample receiving zone 12, the labeling zone 14, the detection zone 15, and the absorbent zone 20 on the common substrate 22. In the illustrated implementation, a substantial portion of the detection zone 15, including three capture regions 82, 84, 86, is exposed for optical inspection.

In one illustrative example, the labeling zone 14 contains different fluorescent labels (e.g., quantum dots) that specifically bind different respective target analytes that might be present in a sample. The fluorescent labels emit light within different, non-overlapping wavelength ranges. In this example, the capture regions 82 and 84 are test regions that contain different immobilized reagents that specifically bind respective ones of the target analytes, and the capture region 86 is a control region that contains an immobilized reagent that specifically binds one or more of the labels in the labeling zone 14.

The diagnostic test system 74 includes three optical detectors 76, 78, 80 that are aligned with respective ones of the capture regions 82, 84, 86 when the test strip 75 is loaded within the housing 60 (see FIG. 5). Each of the optical detectors 76-82 includes a respective lens 88, 90, 92, a respective optical filter 94, 96, 98, and a respective pair of baffles 100, 102, 104. When the test strip 75 is loaded in the receptacle 68 of the housing 60 (see FIG. 5), the lenses 88-92 focus the light from the views of the corresponding capture regions 82-86 onto the active areas of the optical detectors 76-80. The optical filters 94-98 are configured to selectively transmit light within respective wavelength ranges that encompass the wavelength ranges of light respectively emitted by the fluorescent labels that are respectively immobilized in the capture regions 82-86. The pairs of baffles 100-104 block light that is emitted or reflected from areas outside the corresponding views of the capture regions 82-86 and thereby prevent such light from reaching the active areas of the optical detectors 76-80.

In operation, the light source 72 illuminates the capture regions 82-86 with light 106. The illuminating light 106 may be broadband or narrowband and may be polarized or non-polarized. The optical detectors 76-80 produce respective electrical signals 48 from the portions of the illuminated capture regions 82-86 that are within the respective views of the optical detectors 76-80. In this way, each optical detector 76-80 is able to resolve or separably image a respective localized region of a respective one of the capture regions 82-86. The operation of the optical detectors 76-80 may be synchronized with the operation of the light source 72. For example, the optical detectors 76-80 may produce the electrical signals 48 while the capture regions 82-86 are being illuminated or after they have been illuminated by the light source 72.

Figure 7:
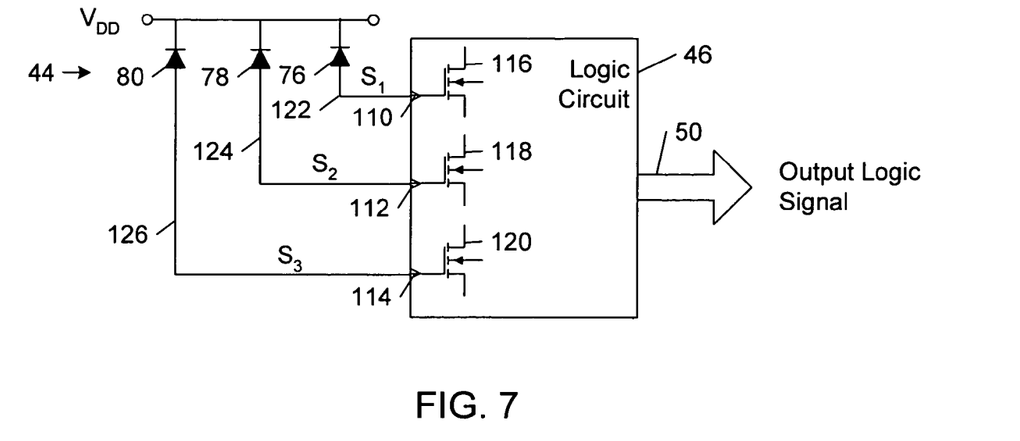
FIG. 7 is a schematic diagram of a portion of an embodiment of the diagnostic test system shown in FIG. 6 in which the optical detectors are coupled between a voltage source and logic inputs of the logic circuit.

FIG. 7 shows an embodiment of the diagnostic test system 74 in which the optical detectors 76-80 are coupled between a voltage source ($V_{DD}$) and the inputs 110, 112, 114 of the logic circuit 46. In this embodiment, the optical detectors 76-80 are implemented by semiconductor photodiodes (e.g., p-i-n photodiodes) and the logic circuit inputs 110-114 correspond to the gate inputs of n-type CMOS transistors 116, 118, 120. In other embodiments, the optical detectors 76-80 may be implemented by a different type of photoresponsive device and the logic circuit inputs 110-114 may correspond to the inputs of different types of circuit elements. In this embodiment, the conditioning circuits are omitted.

In operation, the optical detectors 76-80 produce respective detection signals 122, 124, 126 (also labeled $S_1$, $S_2$, $S_3$) that charge the respective capacitances at the logic circuit inputs 110-114. The transistors 116-120 turn on if the logic circuit inputs 110-114 are charged to a voltage level that exceeds the respective threshold voltages of the transistors 116-120 and the associated source voltages. That is, the transistors 116-120 quantize the detection signals ($S_i$) into respective output logic signals ($OLS_i$) as follows:

$$OLS_i = \text{HIGH if } S_i \geq v_{ti} + v_{si} \quad (1)$$

$$OLS_i = \text{LOW if } S_i < v_{ti} + v_{si} \quad (2)$$

where $v_{ti}$ is the threshold voltage of the transistor i and $v_{si}$ is the bias voltage at the source terminal of the transistor i.

The turn-on voltages at the gates of the transistors 116-120 typically are set to respective levels that separate true detection results (e.g., high logic states) from negative detection results (e.g., low logic states). For example, in some embodiments, the turn-on threshold levels are set so that respective ones of the target analytes are detected (e.g., a true logic state) if the corresponding electrical signals 122-126 turn on the transistors 116-120 within a prescribed period; otherwise, respective ones of the target analytes are not detected (e.g., a false logic state). In general, the turn-on levels at the gates of the transistors 116-120 may be the same or different.

In some embodiments, the turn-on threshold levels of the input logic circuit transistors 116-120 are set by tailoring the gain and/or bias of transistors 116-120. In other embodiments, the turn-on threshold levels are set by conditioning circuits 64 that are coupled between the optical detectors 76-80 and the logic circuit inputs 110-114, as explained below in connection with the embodiments shown in FIGS. 8 and 9.

Figure 8:
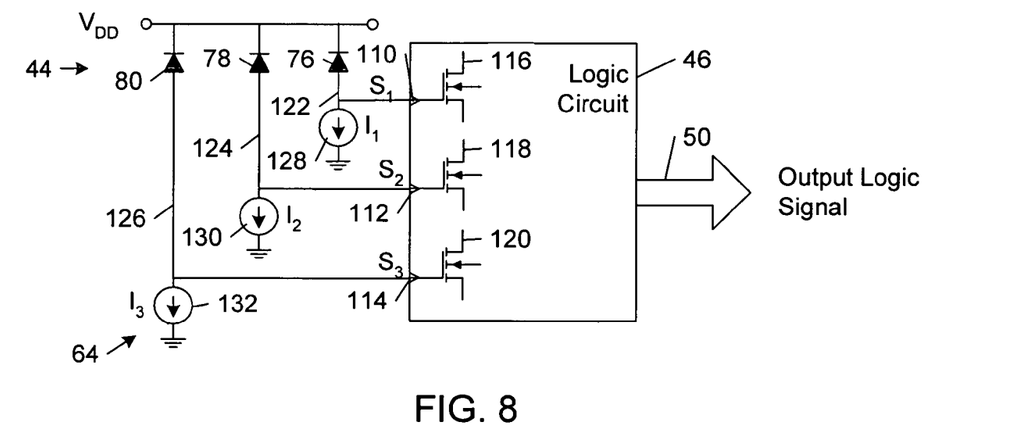
FIG. 8 is a schematic diagram of an embodiment of the diagnostic test system shown in FIG. 7 in which current sources are coupled to outputs of the optical detectors.

FIG. 8 shows an embodiment of the diagnostic test system 74 in which the conditioning circuits 64 include current sources 128, 130, 132 that are respectively coupled to the outputs of the optical detectors 76-80. The current sources 128-132 may be implemented by any type of current source circuit, including a transistor current source, a temperature-compensated current source, and a cascode current source. In general, the amounts (or levels) of source current ($I_1$, $I_2$, $I_3$) that are drawn by the current sources 128-132 may be the same or different. In some embodiments, the source current amounts $I_1$, $I_2$, $I_3$ are set to achieve a desired threshold voltage at the logic circuit inputs 116-120. In some of these embodiments, the source current amounts $I_1$, $I_2$, $I_3$ may be set to achieve specified ratios or weighting factors among the levels of the electrical signals 122-126 that are produced by the optical detectors 76-80. For example, in some embodiments, the source current $I_3$ may be set of a level relative to the source current $I_2$ so that the transistor 120 does not turn on until the optical detector 80 produces twice the amount of current as the amount of current the optical detector 78 must produce in order to turn on the transistor 118. In this way, the source current amounts $I_1$, $I_2$, $I_3$ may be set to achieve a scaled or weighted evaluation of the relationships among the electrical signals produced by the optical detectors 76-80 in accordance with a prescribed assay or screening test.

Figure 9:
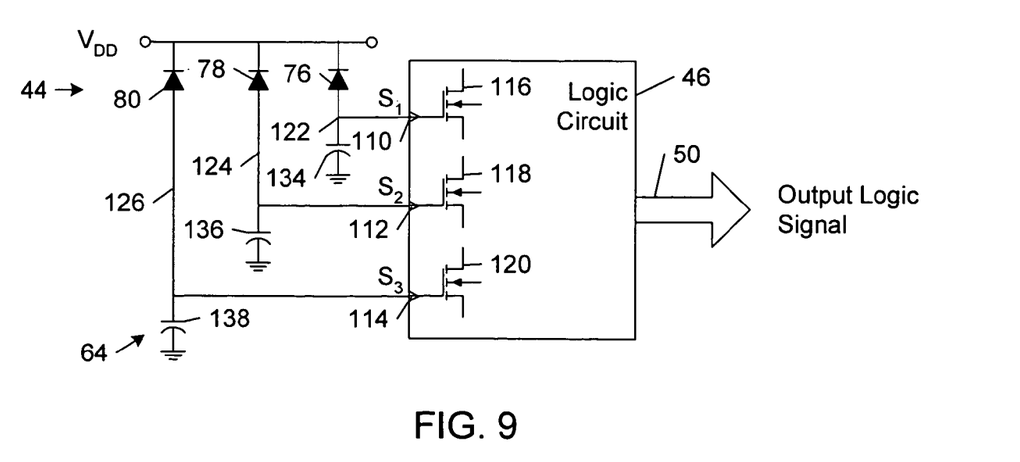
FIG. 9 is a schematic diagram of an embodiment of the diagnostic test system shown in FIG. 7 in which capacitors are coupled to outputs of the optical detectors.

FIG. 9 shows an embodiment of the diagnostic test system 74 in which the conditioning circuits 64 include capacitors 134, 136, 138 that are respectively coupled to the outputs of the optical detectors 76-80. In general, the capacitive loads of the capacitors 134-138 may be the same or different. In some embodiments, the capacitive loads are set to achieve a desired threshold voltage at the logic circuit inputs 116-120. In some of these embodiments, the capacitive loads may be set to achieve specified ratios or weighting factors among the levels of the electrical signals 122-126 that are produced by the optical detectors 76-80. For example, in some embodiments, the capacitance of capacitor 138 may be set of a level relative to the capacitance of capacitor 136 so that the transistor 120 does not turn on until the optical detector 80 produces twice the amount of current as the amount of current the optical detector 78 must produce in order to turn on the transistor 118. In this way, the capacitances of the capacitors 134-138 may be set to achieve a scaled or weighted evaluation of the relationships among the electrical signals produced by the optical detectors 76-80 in accordance with a prescribed assay or screening test.

In some embodiments, conditioning circuits 64 perform gating and reset functions that ensure that the detection signals $S_1$, $S_2$, $S_3$ correspond to the desired measurements of light intensity from the test strip 42, as explained below in connection with the embodiments shown in FIGS. 10 and 11.

Figure 10:
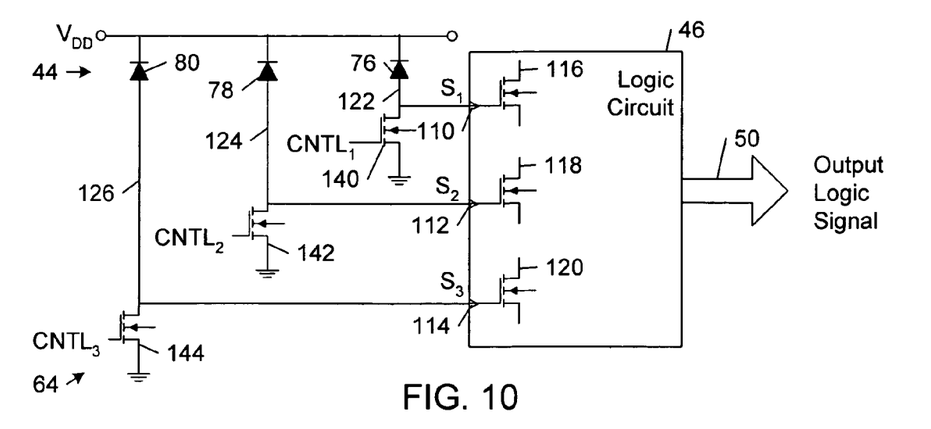
FIG. 10 is a schematic diagram of an embodiment of the diagnostic test system shown in FIG. 7 in which switches are coupled between outputs of the optical detectors and a ground potential.

In the embodiment shown in FIG. 10, the conditioning circuits 64 are implemented by transistors 140, 142, 144 that selectively couple the outputs of the optical detectors 76-80 to an electric charge sink (e.g., a ground source potential) in response to control signals ($CNTL_1$, $CNTL_2$, $CNTL_3$) that are produced by the controller 62 (see FIG. 5). This feature allows the controller 62 to establish a reset period when the transistors 140-144 are turned on and a reading period when the transistors 140-144 are turned off. In some embodiments, the light source 72 (FIG. 5) is operable to illuminate one or more of the views in the receptacle 68, and the controller synchronizes the illumination of the one or more views with the reading period (e.g., the light source 72 is turned on during the reading period and turned off during other periods). During the reset period, any electric charge on the logic circuit inputs 110-114 are discharged through the transistors 140-144 to ground potential. During the reading period, the optical detectors 76-80 charge the logic gate inputs 110-114 to respective levels that reflect success or failure of the optical detectors to detect target analyte labels in the capture regions of the test strip 42.

Figure 11:
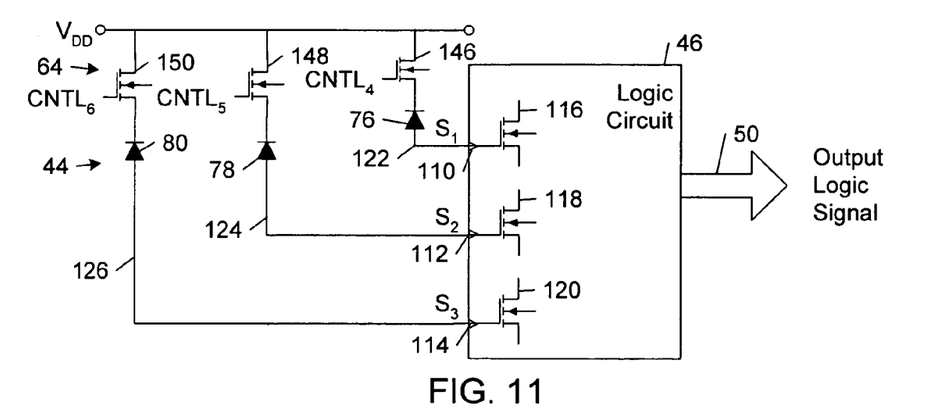
FIG. 11 is a schematic diagram of a portion of an embodiment of the diagnostic test system shown in FIG. 7 in which switches are coupled between the voltage source and the optical detectors.

In the embodiment shown in FIG. 11, the conditioning circuits 64 are implemented by transistors 146, 148, 150 that selectively couple the inputs of the optical detectors 76-80 to the voltage source $V_{DD}$ in response to control signals ($CNTL_4$, $CNTL_5$, $CNTL_6$) that are produced by the controller 62 (see FIG. 5). This feature allows the controller 62 to establish a discharge period when the transistors 146-150 are turned off and a reading period when the transistors 146-150 are turned on. During the discharge period, the optical detectors 76-80 are in photo-voltaic mode and any electric charge on the logic circuit inputs 110-114 are discharged by leakage currents. During the reading period, the optical detectors 76-80 charge the logic gate inputs 110-114 to respective levels that reflect success or failure of the optical detectors to detect target analyte labels in the capture regions of the test strip 42. Transistors 146, 148, 150 can be on either side of (i.e., in series with) the optical detectors and the logic circuit inputs.

Figure 12:
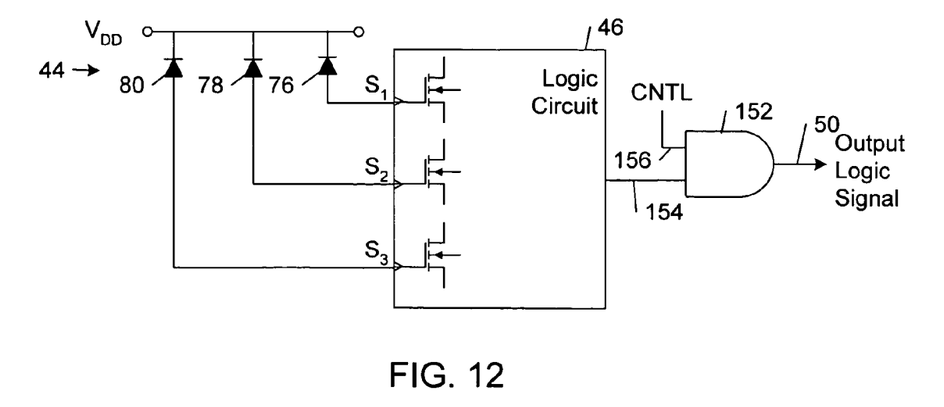
FIG. 12 is a schematic diagram of an embodiment of the diagnostic test system shown in FIG. 7 in which a logic gate is coupled to receive an output logic signal from the logic circuit and a control signal from a controller.

In the embodiment shown in FIG. 12, an AND logic gate 152 has a first input 154 coupled to the output of the logic circuit 46, a second input 156 coupled to receive a control signal (CNTL) from the controller 62 (see FIG. 5), and an output that produces the output logic signal 50. In this embodiment, the controller 62 establishes the reset period by setting the CNTL signal low, in which case the output logic signal 50 will be low, and establishes the reading period by setting the CNTL signal high, in which case the output logic signal 50 will track the output signal of the logic circuit 46 that is applied to the first input 154 of the AND logic gate 152.

Figure 13:
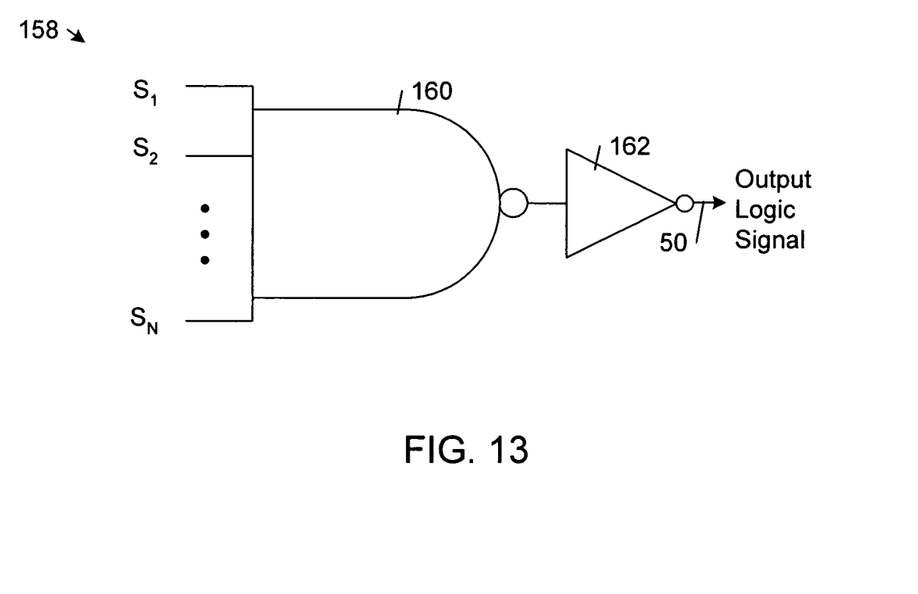
FIG. 13 is a schematic diagram of an AND logic circuit producing an output logic signal from a set of N input detection signals.

FIG. 13 shows an embodiment 158 of the logic circuit 46 that includes a NAND logic gate 160 and an inverter 162, which together implement an AND logic function. In particular, the output logic signal 50 is in a high logic state only when the detection signals $S_1$, $S_2$, ... $S_N$ all are in the high logic state (e.g., are sufficient to turn on all the input transistors of the logic circuit 158 during the reading period); otherwise the output logic signal 50 is in the low logic state. The logic circuit 158 may be used, for example, to assay test strips in accordance with a multifactor screening test in which each of a prescribed set of target analytes must be present in a sample to yield a positive test result (e.g., the output logic signal 50 is in the high logic state).

Figure 14:
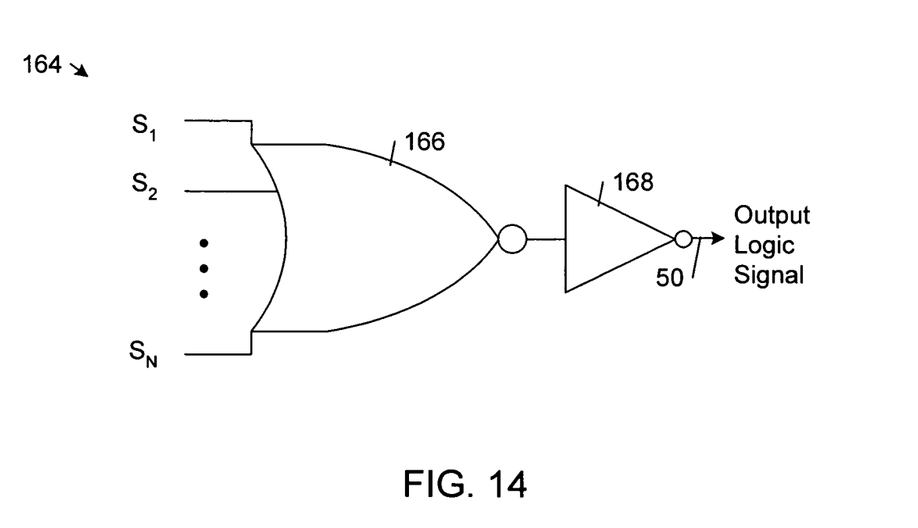
FIG. 14 is a schematic diagram of an OR logic circuit producing an output logic signal from a set of N input detection signals.

FIG. 14 shows an embodiment 164 of the logic circuit 46 that includes a NOR logic gate 166 and an inverter 168, which together implement an OR logic function. In particular, the output logic signal 50 is in a high logic state when any of the detection signals $S_1, S_2, \ldots S_N$ is in the high logic state (e.g., is sufficient to turn on any of the input transistors of the logic circuit 158 during the reading period). The output logic signal 50 is in the low logic state only when all the detection signals $S_1, S_2, \ldots S_N$ are in the low logic state. The logic circuit 158 may be used, for example, to assay test strips in accordance with a multifactor screening test in which only one of a prescribed set of target analytes must be present in a sample to yield a positive test result (e.g., the output logic signal 50 is in the high logic state).

IV. Conclusion

The embodiments that are described above provide systems and methods of performing rapid, low-cost multifactor assays on test strips that have different types of capture reagents. These embodiments enable test strips to be evaluated in terms of logical relationships among the detection results for different target analytes on a single test strip. Exemplary assays of this type include screening tests for drugs of abuse, screening tests for prescription medicines, and screening tests for multifactor clinical scenarios, such as diseases, allergies, and chemical sensitivities.

Other embodiments are within the scope of the claims.

What is claimed is:

1. A diagnostic test system, comprising:
   a receptacle;
   an assay test strip positioned in the receptacle and having multiple capture regions which specifically bind to one or more target analytes and which produce a light when the target analyte is immobilized in the capture region;
   a plurality of optical detectors each having a corresponding view of a capture region and adapted to produce an electrical signal at a respective detector output in response to light produced from at least a portion of the capture region;
   signal conditioning circuits coupled between respective ones of the detector outputs and respective ones of logic inputs; and
   a logic circuit comprising:
   a plurality of logic inputs respectively coupled to the signal conditioning circuits; and
   transistors respectively coupled to the plurality of logic inputs, wherein the transistors turn on if the logic circuit inputs are charged to a voltage level that exceeds a threshold voltage of the transistors;
   wherein the logic circuit is configured to produce at least one output logic signal that corresponds to a logical combination of electrical signals produced from the capture regions and received at the plurality of logic inputs.

2. The diagnostic test system of claim 1, wherein each of the optical detectors comprises at least one photodetector and at least one optical element intercepting light from the corresponding view.

3. The diagnostic test system of claim 1, wherein the logic circuit comprises at least one logic gate.

4. The diagnostic test system of claim 3, wherein the at least one logic gate comprises at least one of a NAND logic gate and a NOR logic gate.

5. The diagnostic test system of claim 1, wherein ones of the signal conditioning circuits comprise respective circuit elements that contribute to setting respective thresholds between logic states at respective ones of the logic inputs.

6. The diagnostic test system of claim 5, wherein ones of the circuit elements comprise respective capacitors.

7. The diagnostic test system of claim 5, wherein ones of the circuit elements comprise respective current sources.

8. The diagnostic test system of claim 5, wherein ones of the signal conditioning circuits comprise switches coupled between respective ones of the detector outputs and an electric charge sink.

9. The diagnostic test system of claim 1, further comprising a controller coupled to the logic circuit and operable to establish a reading period during which the logic circuit produces the output logic signal.

10. The diagnostic test system of claim 9, further comprising one or more switches coupled in series with respective ones of the photodetectors and a voltage source, wherein the controller is coupled to inputs of the one or more switches.

11. The diagnostic test system of claim 9, further comprising a logic gate having a first input coupled to receive the output logic signal and a second input coupled to the controller.

12. The diagnostic test system of claim 9, further comprising a light source coupled to the controller and operable to illuminate one or more of the views in the receptacle, wherein the controller synchronizes the illumination of the one or more views with the reading period.

* * * * *